United States Patent
Reuter et al.

(10) Patent No.: US 12,022,840 B2
(45) Date of Patent: *Jul. 2, 2024

(54) STRAINS OF BACILLUS FOR INHIBITING FOODBORNE PATHOGENS

(71) Applicant: Phibro Animal Health Corporation, Teaneck, NJ (US)

(72) Inventors: Christopher J. Reuter, Parrish, FL (US); Steven J. MacKenzie, Sarasota, FL (US); Lauren G. Danielson, Bradenton, FL (US); Vincent Scuilla, Sarasota, FL (US)

(73) Assignee: Phibro Animal Health Corporation, Teaneck, NJ (US)

( * ) Notice: Subject to any disclaimer, the term of this patent is extended or adjusted under 35 U.S.C. 154(b) by 997 days.

This patent is subject to a terminal disclaimer.

(21) Appl. No.: 16/797,172

(22) Filed: Feb. 21, 2020

(65) Prior Publication Data

US 2020/0178548 A1    Jun. 11, 2020

Related U.S. Application Data

(63) Continuation of application No. 14/208,959, filed on Mar. 13, 2014, now Pat. No. 10,716,310.

(51) Int. Cl.
*A23B 4/22* (2006.01)
*A61K 35/742* (2015.01)

(52) U.S. Cl.
CPC .............. *A23B 4/22* (2013.01); *A61K 35/742* (2013.01); *Y02A 50/30* (2018.01)

(58) Field of Classification Search
CPC ........ A23B 4/22; A61K 35/742; Y02A 50/30; A61P 31/04; A61P 31/00
See application file for complete search history.

(56) References Cited

U.S. PATENT DOCUMENTS

| | | |
|---|---|---|
| 6,291,426 B1 | 9/2001 | Heins et al. |
| 6,498,137 B1 | 12/2002 | Schalitz et al. |
| 8,236,549 B2 | 8/2012 | Kang et al. |
| 8,338,160 B2 | 12/2012 | Tzeng et al. |
| 8,377,455 B2 | 2/2013 | Ceri et al. |
| 8,404,476 B2 | 3/2013 | Fernandez Martinez et al. |
| 9,253,988 B2 * | 2/2016 | Reuter ..................... A62D 3/00 |
| 9,307,770 B2 * | 4/2016 | Reuter ..................... C12N 1/205 |
| 10,716,310 B2 * | 7/2020 | Reuter ..................... A61P 31/04 |
| 2003/0106499 A1 | 6/2003 | Yamada |
| 2004/0009160 A1 | 1/2004 | Villamar et al. |
| 2005/0031732 A1 | 2/2005 | Suhr-Jessen et al. |
| 2010/0021576 A1 * | 1/2010 | Chang ..................... C12N 1/205 435/252.5 |
| 2012/0177620 A1 | 7/2012 | Farmer |
| 2012/0328572 A1 * | 12/2012 | Terhune .................. A61P 31/00 424/93.46 |
| 2013/0136695 A1 | 5/2013 | Hargis et al. |

FOREIGN PATENT DOCUMENTS

WO    WO 2003/103692    12/2003

OTHER PUBLICATIONS

Suhalim, R et al. Survival of *Escherichia coli* O157:H7 in channel catfish pond and holding tank water. LWT. 2008. 41(6): 1116-1121. (Year: 2008).*
Costa, RA. *Escherichia coli* in seafood: a brief overview. Advances in Bioscience and Biotechnology. 2013. 4: 450-454. Published online Mar. 2013. (Year: 2013).*
Charyulu et al., "Antimicrobial activity of secondary metabolite from marine isolate *Pseudomonas* sp. against Gram positive and negative bacterial including MRSA," *Indian Journal of Experimental Biology* 47:964-968, Dec. 2009.
Li et al., "Beneficial effects of Bacillus licheniformis on the intestinal microflora and immunity of the white shrimp, Litopenaeus vannamei," *Biotechnology Letters* 29:252-530, 2007.
Maketon et al., "Efficacies of some beneficial bacterial on the colonization and inhibition of Vibrio harveyi in black tiger shrimp (*Penaeus monodon Fabricus*) larvae," *Kasetsart Journal (Natural Science)* 38:393-399, 2004.
Tinh et al., "A review of the functionality of probiotics in the larviculture food chain," *Marine Biotechnology* 10(1): 1-12, Jan. 2009.
Vinoj et al., "Inhibitory effects of Bacillus licheniformis (DAB1) and Pseudomonas aeruginosa (DAP1) against Vibrio parahaemolyticus isolated from Fenneropenaeus indicus," *Aquaculture International* 21:1121-1135, 2013.

* cited by examiner

*Primary Examiner* — David W Berke-Schlessel
*Assistant Examiner* — Susan E. Fernandez
(74) *Attorney, Agent, or Firm* — Klarquist Sparkman, LLP

(57) ABSTRACT

A process for inhibiting foodborne pathogens and reducing foodborne disease involves contacting a living animal, a dressed carcass, or a cut of meat with an effective amount of a *bacillus* strain exhibiting antibacterial activity. Strains of antibacterial *bacillus* that are particularly effective for inhibiting *Vibrio* were discovered. These include Bacillus licheniformis OBT 618 and Bacillus amyloliquefaciens OBT 712.

16 Claims, 5 Drawing Sheets

Specification includes a Sequence Listing.

```
                    B licheniformos-HB8-16S-rRNA-seq fasta
>B.licheniformos HB8
TGGAGAGTTTGATCCTGGCTCAGGACGAACGCTGGCGGCGTGCCTAATACATGCAAGTCGAGCGGACCGACGGGAGCTTGCTCC
CTTAGGTCAGCGGCGGACGGGTGAGTAACACGTGGGTAACCTGCCTGTAAGACTGGGATAACTCCGGGAAACCGGGGCTAATAC
CGGATRCTTGATTGAACCGCATGGTTCAATTATAAAAGGTGGCTTTTAGCTACCACTTACAGATGGACCCGCGGCGCATTAGCT
AGTTGGTGAGGTAACGGCTCACCAAGGCAACGATGCGTAGCCGACCTGAGAGGGTGATCGGCCACACTGGGACTGAGACACGGC
CCAGACTCCTACGGGAGGCAGCAGTAGGGAATCTTCCGCAATGGACGAAAGTCTGACGGAGCAACGCCGCGTGAGTGATGAAGG
TTTTCGGATCGTAAAACTCTGTTGTTAGGGAAGAACAAGTACCGTTCGAATAGGGCGGTACCTTGACGGTACCTAACCAGAAAG
CCACGGCTAACTACGTGCCAGCAGCCGCGGTA
```

FIGURE 1

B_amyloliquefaciens-OB5-16S-rRNA-seq.fasta
>B.amyloliquefaciens OB5
TGGAGAGTTTGATCCTGGCTCAGGACGAACGCTGGCGGCGTGCCTAATACATGCAAGTCGAGCGGACAGATGGGAG
CTTGCTCCCTGATGTTAGCGGCGGACGGGTGAGTAACACGTGGGTAACCTGCCTGTAAGACTGGGATAACTCCGGG
AAACCGGGGCTAATACCGGATGGTTGTTTGAACCGCATGGTTCAGACATAAAAGGTGGCTTCGGCTACCACTTACA
GATGGACCCGCGGCGCATTAGCTAGTTGGTGAGGTAACGGCTCACCAAGGCrACGATGCGTAGCCGACCTGAGAGG
GTGATCGGCCACACTGGGACTGAGACACGGCCCAGACTCCTACGGGAGGCAGCAGTAGGGAATCTTCCGCAATGGA
CGAAAGTCTGACGGAGCAACGCCGCGTGAGTGATGAAGGTTTTCGGATCGTAAAGCTCTGTTGTTAGGGAAGAACA
AGTGCCGTTCAAATAGGGCGGCACCTTGACGGTACCTAACCAGAAAGCCACGGCTAACTACGTGCCAGCAGCCGCG
GTA

FIGURE 2

STRAINS OF BACILLUS FOR INHIBITING FOODBORNE PATHOGENS

CROSS REFERENCE TO RELATED APPLICATION

This application is a continuation of U.S. patent application Ser. No. 14/208,959, filed on Mar. 13, 2014, which is incorporated herein by reference in its entirety.

FIELD OF THE DISCLOSURE

This disclosure relates to the use of *bacillus* strains to inhibit the growth, reproduction or propagation of foodborne pathogens to improve good safety and reduce incidents of disease such as gastroenteritis.

BACKGROUND OF THE DISCLOSURE

Foodborne disease caused by contamination from pathogenic bacterial is likely responsible for millions of illnesses annually (at least about 8 million in the United States of America annually according to CDC 2011 estimates), thousands of which result in hospitalization annually, and about 1000 fatalities annually. Foodborne disease generally occurs with at least a similar frequency throughout the world and is the leading cause of illness and death in certain parts of the world.

Known antibacterial agents such as alcohols, chlorine, peroxides, aldehydes, triclosan, triclocarban, and benzalkonium chloride are suitable for use in foods due to their inherent toxicity. Treatment with gaseous antibacterial agents (such as ozone or ethylene oxide) or irradiation (such as with ionizing radiation or x-rays) can be safe, effective and economically advantageous in certain cases, but are not favorably perceived by the public. Such techniques have been criticized by public interest groups and public health experts for various reasons, including allegations that these techniques can mask food spoilage, discourage adherence to good food processing practices, kill beneficial bacterial (e.g., probiotics), denature or degrade nutrients, impair flavor and leave bacterial toxins that were present before the treatment.

*Bacillus* trains exhibiting antifungal activity and the use of such bacterial to control plant diseases are described in the literature (e.g., U.S. Pat. No. 6,291,426).

Antibacterial activity of secondary metabolites obtained from *Pseudomonas* strains has been reported in the literature (e.g., Madhava Charyulu et al., Indian Journal of Experimental Biology, Vol. 47, December 2009, pp. 964-968). It was proposed that such secondary metabolites could be useful in new drugs such as antimicrobial drugs.

Accordingly, new and effective methods of reducing foodborne disease are desired.

SUMMARY OF THE DISCLOSURE

Disclosed is a method of inhibiting foodborne pathogens and thereby reducing foodborne disease by applying to or feeding to a living animal, an animal carcass or to cuts of meat an effective amount of a *bacillus* strain exhibiting antibacterial activity.

Also disclosed are specific strains of antibacterial bacilli that are particularly effective in inhibiting *Vibrio*. These include *Bacillus licheniformis* OBT 618, characterized by the sequence shown in FIG. 1 and *Bacillus amyloliquefaciens* OBT 712, characterized by the sequence shown in FIG. 2.

BRIEF DESCRIPTION OF THE DRAWINGS

FIG. 1 (SEQ. ID NO: 1) is the relevant sequence for *Bacillus licheniformis* OBT 618.

FIG. 2 (SEQ. ID NO: 2) is the relevant sequence listing for *Bacillus amyloliquefaciens* OBT 712.

DEPOSIT OF BIOLOGICAL MATERIAL

Figure 3:
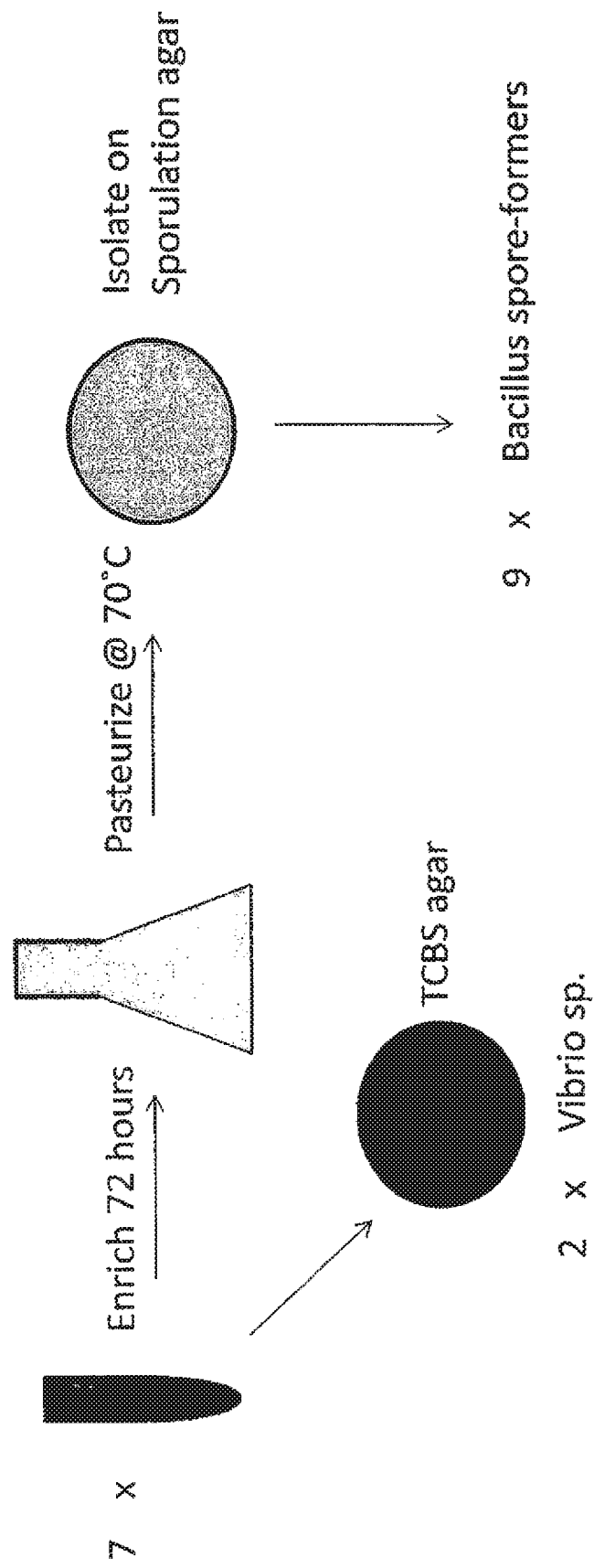
FIG. 3 is a schematic illustration of the preparation of antibacterial *bacillus* strain isolate.

The following biological materials have been deposited under the terms of the Budapest Treaty with the American Type Culture Collection, 10801 University Boulevard, Manassas, Virginia, 20110, (ATCC) and given the following deposit designation numbers:

PTA-122189 —*Bacillus amyloliquefaciens* strain OBT-712 deposited on May 29, 2015; and PTA-122188 —*Bacillus licheniformis* strain OBT-618 deposited on May 29, 2015. The *Bacillus* strains were deposited under conditions that assure that access to the bacteria will be available during the pendency of this patent application to one determined by the Commissioner of Patents and Trademarks to be entitled thereto under 37 C.F.R. § 1.14 and 35 U.S.C. § 122. The deposits represent substantially pure samples of each of the *Bacillus* strains. The deposits are available as required by foreign patent laws in countries wherein counterparts of the subject application, or its progeny, are filed. All restrictions on the availability to the public of the material so deposited will be irrevocably removed upon the granting of a patent. However, it should be understood that the availability of a deposit does not constitute a license to practice the subject invention in derogation of patent rights granted by governmental action.

DESCRIPTION OF THE DISCLOSED EMBODIMENTS

It has been discovered that foodborne pathogens can be inhibited when contact with an effective amount of a *bacillus* strain exhibiting antibacterial activity.

The term "inhibit" means to reduce or arrest growth and/or reproduction of bacterial pathogens that can cause foodborne diseases, and encompasses killing such bacterial pathogens.

The term "effective amount" means an amount that will achieve a desired level of foodborne pathogen inhibition to effect a beneficial result such as reducing bacterial pathogen populations in or on food, or in or on animals that are processed into food.

Foodborne pathogens that can be inhibited include *Salmonella enteric, Escherichia coli, Clostridium difficile* and *Vibrio*.

*Bacillus* strains exhibiting antibacterial activity include *Bacillus licheniformis* strains (e.g., OBT 618), and *Bacillus amyloliquefaciens* strains (e.g., OBT 712). The relevant sequence listings for *Bacillus licheniformis* OBT 618 and *Bacillus amyloliquefaciens* OBT 712 are shown in FIGS. 1 and 2, respectively.

The step of contacting the foodborne pathogens with a *bacillus* strain exhibiting antibacterial activity can involve application of an aqueous based composition containing the antibacterial *bacillus* train to a live animal, a dressed carcass or cuts of meat, such as by spraying, brushing or dipping. In the case of aquatic animals, the antibacterial *bacillus* strain can be added to a container, tank or enclosure (e.g., a fish hatchery) in which the aquatic animals are raised and/or from which they are harvested. As another alternative, contact between the bacterial pathogens and the antibacterial *bacillus* can be achieved by feeding the antibacterial *bacillus* to the animal, either directly or to animals that serve as the food source for the animal that is ultimately processed for consumption such as by a human or companion animal.

FIG. 3 shows a method of preparing an antibacterial *bacillus* strain isolate. Samples from marine environments were selected from spore-forming *bacillus* and *Vibrio* species. The *bacillus* samples were enriched, and subsequently pasteurized at about 70° C. *Bacillus* isolates were then placed on sporulation agar. The *Vibrio* was placed on thio-sulfate-citrate-bile salts-sucrose (TCBS) agar.

Figure 4:
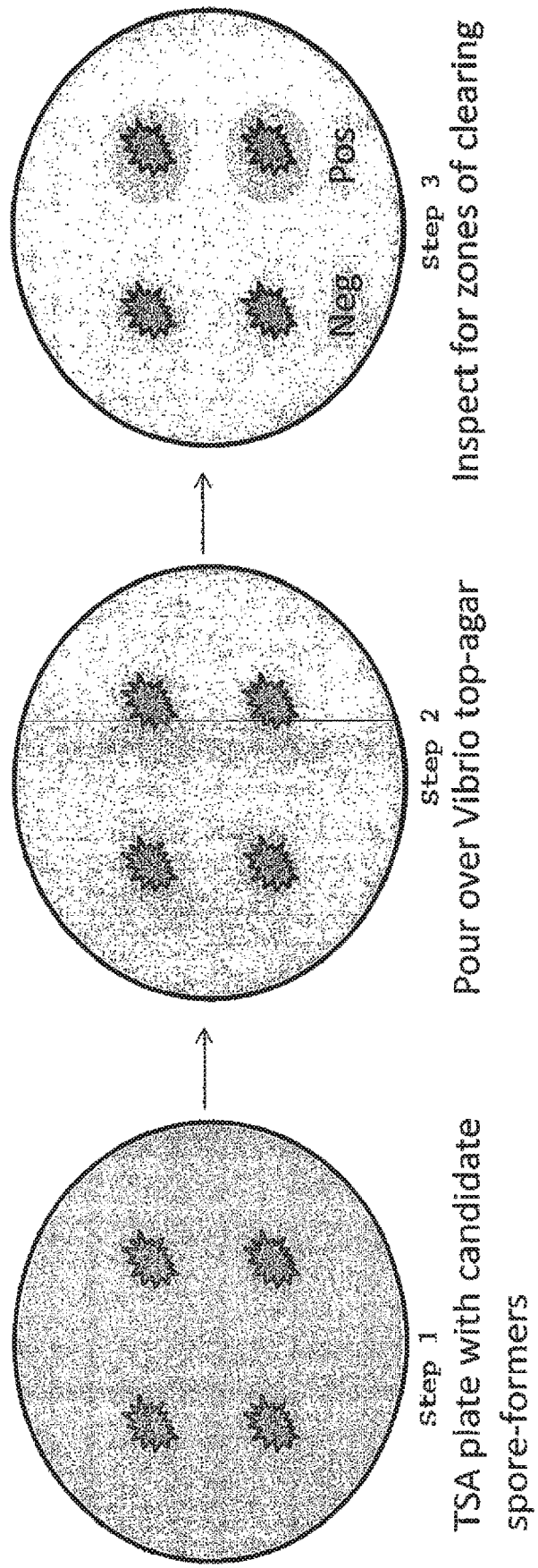
FIG. 4 is a schematic illustration of a process for screening isolates that are antagonistic toward an isolate of *Vibrio* sp. selected from a marine environment using an agar overlay method.

FIG. 4 shows an assay to determine growth inhibition for the *bacillus* strains. A candidate *bacillus* spore-former is placed on a trypticase soy agar (TSA) plate, and thereafter, *Vibrio* isolate embedded in top agar is disposed over the TSA plate. After a sufficient period (e.g., two days), the zones in which the candidate *bacillus* strains are overlaid with the *Vibrio* isolates are inspected for clearance of the *Vibrio*. Positive results are illustrated on the right side of the agar dish at Step 3 of FIG. 4.

Figure 5:
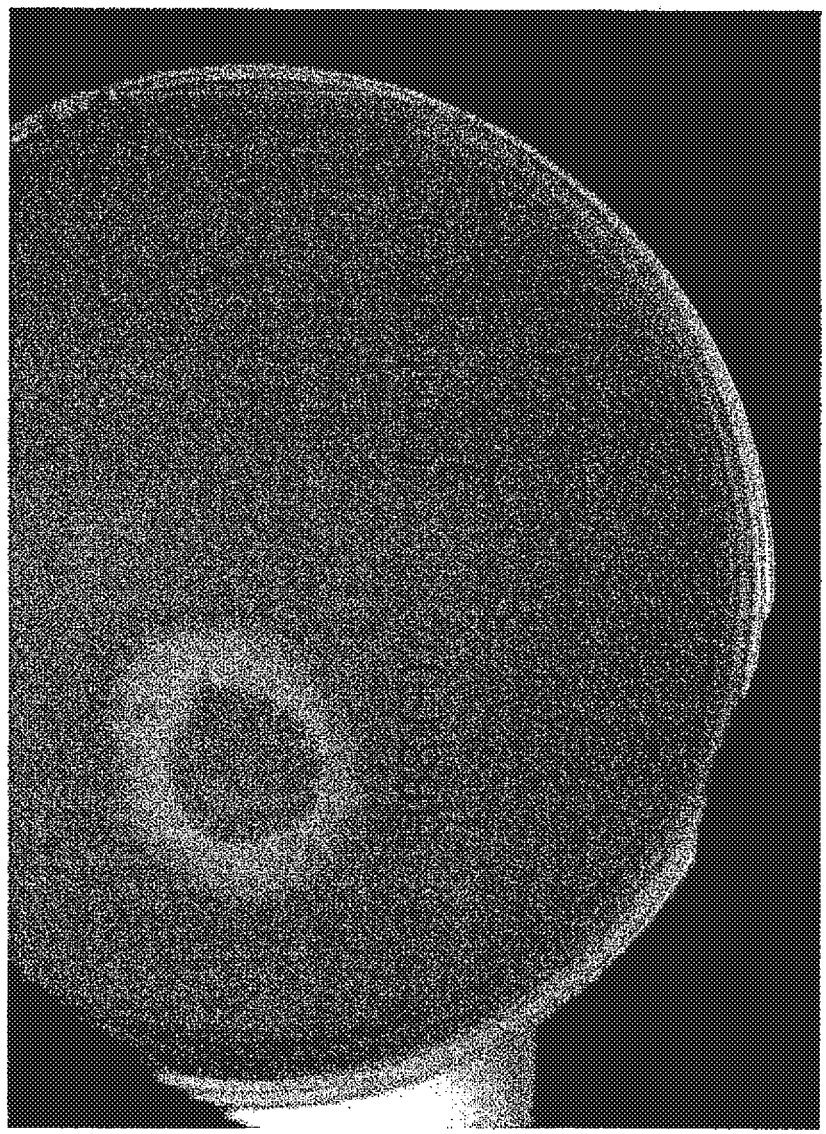
FIG. 5 is a photograph showing a comparison of a positive ("+") result for *Bacillus amyloliquefaciens* OBT 712 to a negative ("−") control.

FIG. 5 is a photograph showing an actual positive result labeled "HB8(+)" and a negative result labeled "Control(−)."

Isolates were screened for antagonism toward an isolate of *Vibrio* sp. selected from a marine environment using an agar overlay method. This method consisted of covering one day old *bacillus* cultures with the *Vibrio* isolate embedded in agar. Zones of clearance were evaluated at 2 days. Thirty-six isolates from various environments were screened. Of the thirty-six isolates tested, two isolates, a *B. licheniformis* (OBT 618) and a *B. amyloliquefaciens* (OBT 712), had particularly high levels of antagonism toward *Vibrio*. All strains are easily propagated on trypticase soy agar (TSA) and sporulate in liquid medium.

These strains are antagonistic to *Vibrio*. They produce a clearance zone on agar plates when the *Bacillus* colonies are covered with a thin agar layer that includes *Vibrio* sp. One isolate has a delayed response killing the *Vibrio* after it has grown. The other inhibits *Vibrio* growth.

In a preliminary trial, feeding rotifers the *Bacillus* strains increased survivability of larval snook fed the rotifers. The mechanism by which the *Bacillus* isolates fed to rotifers increases survivability of larval snook fed the rotifers has not been determined. It is conceivable that they are inhibiting growth of *Vibrio* within the digestive tract of rotifers or snook. It is also possible that they inhibit growth of *Vibrio* within larval brooding tanks overall.

Anticipated use is at a concentration of $10^5$-$10^7$ spores/ml in live food tanks or in a larval rearing tank. They are stored as freeze dried spores. Spores can be supplied on a nutritive carrier.

The invention could possibly be used to suppress *Vibrio* sp. on multiple fish species as well as shell fish that are grown in culture. *Vibrio* is a gammaproteobacteria, a class of bacterial that includes *Pseudomonas* and *Enterobacter* such as *E. coli* and *Salmonella* sp. It could potentially be antagonistic to these other species.

Possible ancillary benefits of *Bacillus* addition in aquaculture include improved nutrient availability and waste reduction.

The *Bacillus licheniformis* strain OBT 618 was deposited under the Budapest Treaty and will be irrevocably and without restriction or condition released to be public upon issuance of a patent. The *Bacillus licheniformis* strain OBT 618 deposited May 29, 2015 at the American Type Culture Collection (ATCC), P.O. Box 1549, Manassas, Virginia 20109 and given accession number PTA-122188.

The described embodiments are preferred and/or illustrated, but are not limiting. Various modifications are considered within the purview and scope of the appended claims.

What is claimed is:

1. A process, comprising contacting a living animal, dressed carcass, or cut of meat with an effective amount of *Bacillus licheniformis* strain OBT 618 as deposited with the American Type Culture Collection under accession number PTA-122188 that exhibits antibacterial activity,
    wherein the process is a process for producing a food product, and the effective amount is an amount for inhibiting at least one foodborne pathogen.

2. The process of claim 1, in which the at least one foodborne pathogen is present in or on the living animal, dressed carcass, or cut of meat.

3. The process of claim 2, in which the at least one foodborne pathogen comprises *Salmonella enteric, Escherichia coli, Clostridium difficile, Vibrio*, or a combination thereof.

4. The process of claim 2, wherein the at least one foodborne pathogen is *Salmonella enteric, Escherichia coli* and/or *Clostridium difficile*.

5. The process of claim 4, in which contacting the living animal, dressed carcass, or cut of meat with the *Bacillus licheniformis* strain OBT 618 is done by applying an aqueous based composition containing the *Bacillus licheniformis* strain OBT 618 to the live animal, dressed carcass, or cut of meat.

6. The process of claim 5, in which the applying is done by spraying, brushing or dipping.

7. The process of claim 4, in which the process is performed on a living animal, and the contacting is done by feeding the *Bacillus licheniformis* strain OBT 618 to the living animal.

8. The process of claim 4, wherein the at least one foodborne pathogen is *Salmonella enteric*.

9. The process of claim 4, wherein the at least one foodborne pathogen is *Escherichia coli*.

10. The process of claim 1, in which contacting the living animal, dressed carcass, or cut of meat with the *Bacillus licheniformis* strain OBT 618 is done by applying an aqueous based composition containing the *Bacillus licheniformis* strain OBT 618 to the live animal, dressed carcass, or cut of meat.

11. The process of claim 10, in which the applying is done by spraying, brushing or dipping.

12. The process of claim 1, in which the process is performed on a living animal, and the contacting is done by feeding the *Bacillus licheniformis* strain OBT 618 to the living animal.

13. The process of claim 1, in which the process is performed on a living animal, wherein the living animal is a fish or a shell fish contained in a tank holding water, and wherein the *Bacillus licheniformis* strain OBT 618 is added to the water in the tank in the form of spores.

14. The process of claim 13, in which a concentration of *Bacillus licheniformis* strain OBT 618 spores in the water is from $10^5$ to $10^7$ spores/ml.

15. The process of claim 1, comprising:
    feeding the *Bacillus licheniformis* strain OBT 618 to a first animal; and
    feeding the first animal to a second animal, thereby increasing the survivability of the second animal.

16. The process of claim 15, in which the second animal is an aquatic animal and the first animal that is ted to the second animal is a rotifer.

* * * * *

SEQUENCE LISTING

<160> NUMBER OF SEQ ID NOS: 2

<210> SEQ ID NO 1
<211> LENGTH: 536
<212> TYPE: DNA
<213> ORGANISM: Bacillus licheniformis

<400> SEQUENCE: 1

```
tggagagttt gatcctggct caggacgaac gctggcggcg tgcctaatac atgcaagtcg      60
agcggaccga cgggagcttg ctcccttagg tcagcggcgg acgggtgagt aacacgtggg     120
taacctgcct gtaagactgg gataactccg ggaaaccggg gctaataccg gatrcttgat     180
tgaaccgcat ggttcaatta taaaaggtgg cttttagcta ccacttacag atggacccgc     240
ggcgcattag ctagttggtg aggtaacggc tcaccaaggc aacgatgcgt agccgacctg     300
agagggtgat cggccacact gggactgaga cacggcccag actcctacgg gaggcagcag     360
tagggaatct tccgcaatgg acgaaagtct gacggagcaa cgccgcgtga gtgatgaagg     420
ttttcggatc gtaaaactct gttgttaggg aagaacaagt accgttcgaa tagggcggta     480
```

-continued

```
ccttgacggt acctaaccag aaagccacgg ctaactacgt gccagcagcc gcggta        536

<210> SEQ ID NO 2
<211> LENGTH: 535
<212> TYPE: DNA
<213> ORGANISM: Bacillus amyloliquefaciens

<400> SEQUENCE: 2
tggagagttt gatcctggct caggacgaac gctggcggcg tgcctaatac atgcaagtcg     60
agcggacaga tgggagcttg ctccctgatg ttagcggcgg acgggtgagt aacacgtggg    120
taacctgcct gtaagactgg gataactccg ggaaaccggg gctaataccg gatggttgtt    180
tgaaccgcat ggttcagaca taaaaggtgg cttcggctac cacttacaga tggacccgcg    240
gcgcattagc tagttggtga ggtaacggct caccaaggcr acgatgcgta gccgacctga    300
gagggtgatc ggccacactg ggactgagac acggcccaga ctcctacggg aggcagcagt    360
agggaatctt ccgcaatgga cgaaagtctg acggagcaac gccgcgtgag tgatgaaggt    420
tttcggatcg taaagctctg ttgttaggga agaacaagtg ccgttcaaat agggcggcac    480
cttgacggta cctaaccaga aagccacggc taactacgtg ccagcagccg cggta         535
```

UNITED STATES PATENT AND TRADEMARK OFFICE
CERTIFICATE OF CORRECTION

| | |
|---|---|
| PATENT NO. | : 12,022,840 B2 |
| APPLICATION NO. | : 16/797172 |
| DATED | : July 2, 2024 |
| INVENTOR(S) | : Reuter et al. |

It is certified that error appears in the above-identified patent and that said Letters Patent is hereby corrected as shown below:

In the Claims

Column 6, Line 56, "is ted to" should read --is fed to--

Signed and Sealed this
Tenth Day of September, 2024

Katherine Kelly Vidal
*Director of the United States Patent and Trademark Office*